United States Patent
Yano et al.

(10) Patent No.: US 6,299,887 B1
(45) Date of Patent: Oct. 9, 2001

(54) PHOSPHORIC TRIESTERS AND EXTERNAL COMPOSITIONS CONTAINING THE SAME

(75) Inventors: Shinji Yano, Naga-gun; Takashi Komori, Sakura; Shinji Ishikawa, Funabashi; Katsumi Kita, Osaka; Takashi Mizooku, Wakayama, all of (JP)

(73) Assignee: Kao Corporation, Tokyo (JP)

( * ) Notice: Subject to any disclaimer, the term of this patent is extended or adjusted under 35 U.S.C. 154(b) by 795 days.

(21) Appl. No.: 08/606,838

(22) Filed: Feb. 26, 1996

(30) Foreign Application Priority Data

Feb. 24, 1995 (JP) ................................... 7-036680
Jul. 4, 1995 (JP) ................................... 7-168547

(51) Int. Cl.$^7$ .................................................. A61K 7/00
(52) U.S. Cl. .......................... 424/401; 558/208; 558/209; 558/210; 558/213
(58) Field of Search ............................. 424/401; 558/508, 558/209, 210, 213

(56) References Cited

FOREIGN PATENT DOCUMENTS

60163808 * 8/1985 (JP) .

OTHER PUBLICATIONS

JP 4282392 Abstract Oct. 7, 1992.
JP 4202106 Abstract Jul. 22, 1992.
JP 441498 Abstract Feb. 12, 1992.
JP 3123790 Abstract May 27, 1991.
JP 2256624 Abstract Oct. 17, 1990.
JP 193542 Abstract Apr. 12, 1989.
JP 60163808 Abstract Aug. 26, 1985.

* cited by examiner

Primary Examiner—Jyothsna Venkat
(74) Attorney, Agent, or Firm—Oblon, Spivak, McClelland, Maier & Neustadt, P.C.

(57) ABSTRACT

The present invention discloses phosphoric triesters represented by formula (1):

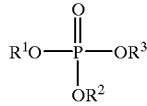

(1)

wherein $R^1$ represents C12–C24 alkyl or alkenyl, $R^2$ represents C6–C24 alkyl, alkenyl, or aryl, and $R^3$ represents C1–C6 alkyl, C2–C6 alkenyl, or aryl; external compositions containing the phosphoric triesters; and methods for preparing asymmetric phosphoric triesters. The compositions of the present invention have excellent compatibility with the skin, good sensation during use, and a high degree of safety.

17 Claims, No Drawings

PHOSPHORIC TRIESTERS AND EXTERNAL COMPOSITIONS CONTAINING THE SAME

BACKGROUND OF THE INVENTION

1. Field of the Invention

The present invention relates to phosphoric triesters which have remarkable compatibility with skin, have excellent feel during use, and are mild to the skin. The invention also relates to external compositions containing the triesters as well as to a method for effectively preparing asymmetric phosphoric triesters.

2. Description of Related Art

Liquid oils are very important and indispensable to cosmetic bases. In addition to performing essential functions such as imparting lubricity to the skin, exhibiting barrier functions by forming hydrophobic films, and suppressing transdermal loss of moisture, liquid oils today are required to 1) be compatible with the skin, 2) provide good sensation when applied to the skin, and 3) be safe to the skin.

In order to meet these requirements, a diversity of new liquid oil bases have been developed and applied in various ways. For example, triglycerides such as squalane, olive oil, etc. are used as sebum analogs for the purpose of providing skin compatibility. Synthetic ester oils such as isopropyl palmitate and isopropyl myristate as well as silicone oils are used to provide the skin with good sensation, due to their low viscosity.

However, these conventional oil bases are problematic in that those having higher polarities which generally accounts for higher skin compatibility tend to have stronger intermolecular forces, resulting in disagreeable sensations, e.g., stickiness, to the skin. Particularly, when ester oils and triglycerides are used, they tend to decompose and cause safety problems, as their compatibility with the skin is enhanced. Moreover, oil bases having low molecular weights also involve crucial problems in safety, although they have relatively good sensation and compatibility with the skin.

On the other hand, lower trialkyl phosphoric esters are already widely used as additives such as plasticizers and stabilizers, as lubricants, or as dispersants due to their excellent characteristics. They are liquid at ambient temperatures, chemically stable, and low in cloud point. They have polarity as well as excellent dissolvability, compatibility, miscibility, and pigment-dispersing ability. However, they are not necessarily satisfactory in terms of safety to the skin. Higher trialkyl esters are reliable in safety, but lack in good sensation as they have high viscosities or high melting points.

As described above, no conventional oil bases meet the following requirements simultaneously: 1) high compatibility with the skin, 2) good sensation during use, and 3) safety to the skin. Thus, liquid oils which fulfill these criteria are still desired.

Under the above circumstances, the present inventors have conducted extensive studies, and have found that the phosphoric triesters represented by the formula (1) described below having certain ester residues have high polarity, excellent compatibility with the skin, low viscosity, and low melting points, and also provide a high degree of safety. The present inventors have also found that compositions containing the phosphoric triesters as liquid oils have excellent compatibility with the skin, good sensation during use, and are very safe. Moreover, in the course of researching of methods for synthesizing these phosphoric triesters, the present inventors have discovered an effective method for preparing asymmetric phosphoric triesters.

SUMMARY OF THE INVENTION

Accordingly, in one aspect of the present invention, there is provided a phosphoric triester represented by the following formula (1):

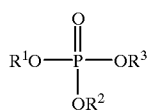

(1)

wherein $R^1$ represents C12–C24 linear or branched alkyl or alkenyl, $R^2$ represents C6–C24 linear, branched, or cyclic alkyl, C6–C24 linear alkenyl, or aryl, and $R^3$ represents C1–C6 linear, branched, or cyclic alkyl, C2–C6 alkenyl, or aryl.

In another aspect of the present invention, there is provided an external composition comprising a phosphoric triester represented by the following formula (1):

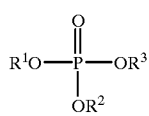

(1)

wherein $R^1$ represents C12–C24 linear or branched alkyl or alkenyl, $R^2$ represents C6–C24 linear, branched, or cyclic alkyl, C6–C24 linear alkenyl, or aryl, and $R^3$ represents C1–C6 linear, branched, or cyclic alkyl, C2–C6 alkenyl, or aryl.

In a further aspect of the present invention, there is provided a method for preparing an asymmetric phosphoric triester comprising the step of adding an alkyl phosphoric halide represented by the following formula (2):

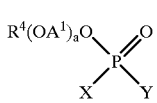

(2)

wherein $R^4$ represents C1–C36 linear or branched alkyl or C2–C36 alkenyl, $A^1$ represents C2–C3 linear or branched alkylene, "a" denotes the average addition mol number of alkylene oxide representing a number from 0 to 20 inclusive, wherein the $A^1$s in the number of "a" may be identical or different from one another, X is a halogen atom or a group represented by $R^5(OA^2)_bO$— (wherein $R^5$ is C1–C36 linear or C2–C36 branched alkyl or alkenyl, $R^4$ and $R^5$ are the same or different from one another, $A^2$ represents C2–C3 linear or branched alkylene group, "b" denotes the average addition mol number of alkylene oxide representing a number from 0 to 20 inclusive, wherein the $A^2$s in the number of "b" may be identical or different from one another), and Y represents a halogen atom, to an alcohol or an alcoholate represented by the following formula (3):

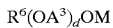 (3)

wherein $R^6$ represents C1–C36 linear or branched alkyl or C2–C36 alkenyl, $A^3$ represents C2–C3 linear or branched alkylene, "d" denotes the average addition mol number of alkylene oxide representing a number from 0 to 20 inclusive, wherein the $A^3$s in the number of "d" are identical or different from one another, and M represents a hydrogen atom, alkali metal, or alkaline earth metal, to cause a reaction, thereby obtaining an asymmetric phosphoric triester represented by the following formula (4):

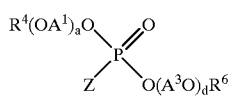
(4)

wherein $R^4$, $R^6$, $A^1$, $A^3$, "a", and "d" respectively have the meanings as defined above, $R^4$ and $R^6$ are different from each other, and Z represents $R^5(OA^2)_bO$— or $R^6(OA^3)_dO$— (wherein $R^5$, $R^6$, $A^2$, $A^3$, "b", and "d" respectively have the meanings as defined above. This method is hereinafter referred to as method (i).

In a further aspect of the present invention, there is provided a method for preparing an asymmetric phosphoric triester comprising the following steps: reacting a phosphorus oxyhalide represented by the following formula (5)

(5)

wherein Y has the same meaning as defined above, with a first organic hydroxyl compound represented by the following formula (6):

$R_4(OA^1)_aOH$ (6)

wherein $R^4$, $A^1$, and "a" have the same meanings as defined above, or with a mixture of the first organic hydroxyl compound and a second organic hydroxyl compound represented by the following formula (7):

$R^5(OA^2)_bOH$ (7)

wherein $R^5$, $A^2$, and "b" have the same meanings as defined above, in the presence of an organic amine, removing a hydrochloric acid salt of the organic amine to obtain an alkyl phosphoric halide represented by the above-described formula (2), and reacting the alkyl phosphoric halide represented by formula (2) with an alcohol or an alcoholate represented by the above-described formula (3) to obtain an asymmetric phosphoric triester represented by the above-described formula (4). This method is hereinafter referred to as method (ii).

In a still further aspect of the present invention, there is provided a method for preparing an asymmetric phosphoric triester comprising the following steps:

reacting a phosphorus oxyhalide of formula (5) with a first organic hydroxyl compound of formula (6) or with a mixture of the first organic hydroxyl compound and a second organic hydroxyl compound of formula (7), removing a hydrochloric acid salt of the organic amine to obtain an alkyl phosphoric halide of formula (2), and adding the alkyl phosphoric halide of formula (2) to an alcohol or an alcoholate of formula (3) to cause a reaction, thereby obtaining an asymmetric phosphoric triester of formula (4). This method is hereafter referred to as method (iii).

The above and other objects, features, and advantages of the present invention will become apparent from the following description.

DETAILED DESCRIPTION OF PREFERRED EMBODIMENTS

In the above-described formula (1), examples of C12–C24 linear alkyl groups represented by $R^1$ include n-dodecyl, n-tetradecyl, n-hexadecyl, and n-octadecyl. Examples of branched alkyl groups include 2-methyldodecyl, 2-methyltetradecyl, 2-butyloctyl, 2-hexyldecyl, 2-heptylundecyl, 2-octyldodecyl, 2-decyltetradecyl, 5,7,7-trimethyl-2-(1,3,3-trimethylbutyl) octyl, as well as isostearyl occurring as a C12–C24 mixture characterized by primarily containing the structure represented by the following formula:

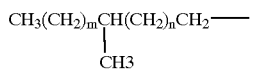

wherein m+n is equal to 14, with a peak occurring at m=n=7 within the distribution of m and n. Such isostearyl groups are prepared by isomerizing a skeleton of a fatty acid derived from beef tallow or tall oil. Examples of alkenyl groups include hexadecenyl, octadecenyl, hexadecadienyl, octadecadienyl, and eicosadienyl. From the viewpoint of mildness to the skin, $R^1$ is preferably C13–C20 branched alkyl or linear alkenyl, more preferably C16–C20 branched alkyl, and particularly preferably the above-mentioned isostearyl, 2-heptylundecyl, or oleyl.

In the above-described formula (1), examples of C6–C24 linear or branched alkyl groups represented by $R^2$ include, in addition to those listed as examples of $R^1$, n-hexyl, n-octyl, n-decyl, and n-ethylhexyl. Examples of cyclic alkyl groups include cyclohexyl, cycloheptyl, cyclooctyl, and cyclododecyl. Examples of linear alkenyl groups include undecenyl, hexadecenyl, octadecenyl, hexadecadienyl, octadecadienyl, and eicosadienyl. Examples of aryl groups include phenyl and naphthyl. From the viewpoint of mildness to the skin, $R^2$ is preferably C6–C20, more preferably C11–C20, and particularly preferably C16–C20 linear or branched alkyl or linear alkenyl groups. Specifically, $R^2$ is preferably C11–C20 (more preferably C16–C20) branched alkyl or linear alkenyl, and particularly preferably the above-mentioned isostearyl, 2-heptylundecyl, and oleyl.

In the above-described formula (1), examples of C1–C6 linear alkyl groups represented by $R^3$ include methyl, ethyl, n-propyl, n-butyl, n-pentyl, and n-hexyl. Examples of branched alkyl groups include isopropyl, isobutyl, secbutyl, and tert-butyl. Examples of cyclic alkyl groups include cyclopentyl and cyclohexyl. Examples of alkenyl groups include allyl and methallyl. Examples of aryl groups include phenyl. From the viewpoints of compatibility with the skin and mildness to the skin, $R^3$ is preferably C1–C6, more preferably C1–C4 linear or branched alkyl groups. Particularly, ethyl is preferred from the viewpoint of low viscosity.

The phosphoric triesters of formula (1) preferably have a C13–C20 branched alkyl or linear alkenyl group for $R^1$, a C11–C18 linear or branched alkyl or alkenyl group for $R^2$ and a C1–C6 linear or branched alkyl group for $R^3$, as such phosphoric triesters have low melting points. As regards the combination of $R^1$ to $R^3$ groups, combinations in which the sum of the carbon numbers of $R^1$, $R^2$, and $R^3$ is from 24 to 40 are more preferred.

The phosphoric triesters of formula (1) can be synthesized by known methods. For example, they can be prepared by reacting a phosphorus oxyhalide such as phosphorus oxychloride with alcohols corresponding to $R^1$, $R^2$, and $R^3$, in a sequential manner, in the absence or presence of a base.

In detail, if R1, $R^2$, and $R^3$ in the target phosphoric triester are different from one another, three different alcohols of $R^1$—OH, $R^2$—OH, and $R^3$—OH, each in an equivalent amount by mol of phosphorus oxyhalide, are sequentially added and reacted. If $R^1$ and $R^2$, or $R^2$ and $R^3$, in the target phosphoric triester are identical, an approximately equivalent amount by mol (or about twice the amount by mol), with respect to phosphorus oxyhalide, of either one of two alcohols is added to phosphorus oxyhalide, and then about twice the amount by mol (or an approximately equivalent amount by mol) of the other alcohol is further added and reacted.

Solvents which are used in the reactions of the present invention are not particularly limited insofar as they are inert in the reaction system and are capable of dissolving phosphorus oxyhalides. Examples of proper solvents include ethers such as tetrahydrofuran and dioxane; aliphatic hydrocarbons such as hexane, heptane, and octane; alicyclic hydrocarbons such as cyclopentane, cyclohexane, and methylcyclohexane; and aromatic hydrocarbons such as benzene, toluene, xylene, and ethylbenzene. These solvents may be used singly or in combinations of two or more. Their amounts are not particularly limited. In general, solvents are used in such amounts that make the concentration of phosphorus oxyhalide not more than 60% by weight, and preferably not more than 30% by weight.

Examples of bases which are used in the reactions of the present invention include organic tertiary amines such as triethylamine, tributylamine, and pyridine; and alkali metal hydroxides such as sodium hydroxide and potassium hydroxide. These bases may be used singly or in combinations of two or more.

The phosphoric triesters of formula (1) can be prepared by the aforementioned known method. As concerns asymmetric phosphoric triesters, better yield can be obtained and the purity of the resulting triesters can be enhanced by using either one of the following method (i) or (ii) for reacting an alkyl phosphoric halide with an alcohol or alcoholate. Method (i): An alkyl phosphoric halide is added to an alcohol or alcoholate so as to cause a reaction. Method (ii): A phosphorus oxyhalide is used as the alkyl phosphoric halide, and the phosphorus oxyhalide is reacted with an organic hydroxyl compound in the presence of an organic amine. From the reaction system, hydrochloric acid salts of the organic amine are removed, and the residue is used in a further reaction.

In the alkyl phosphoric halides of formula (2) which are used in the methods of the present invention, $R^4$ represents C1–C36 linear or branched alkyl or C2–C36 alkenyl groups. $R^4$ is preferably C6–C36 alkyl or alkenyl, and more preferably C6–C20 alkyl. Specific examples of such alkyl or alkenyl groups include hexyl, 2-ethylhexyl, heptyl, octyl, nonyl, decyl, undecyl, dodecyl, tridecyl, tetradecyl, pentadecyl, hexadecyl, heptadecyl, octadecyl, oleyl, elaidyl, eicosyl, isostearyl, as well as a residue obtained by eliminating a hydroxyl group from a higher alcohol such as a C6–C36 linear or branched, saturated or unsaturated alcohol which is obtainable by an oxo process, Ziegler process, or a Guerbet process.

$R^5$ represents C1–C36 linear or branched alkyl or C2–C36 alkenyl. $R^5$ is preferably C1–C20 alkyl or C2–C20 alkenyl, and more preferably C6–C20 alkyl. Specific examples of these alkyl or alkenyl groups include methyl, ethyl, propyl, butyl, pentyl, hexyl, 2-ethylhexyl, heptyl, octyl, nonyl, decyl, undecyl, dodecyl, tridecyl, tetradecyl, pentadecyl, hexadecyl, heptadecyl, octadecyl, oleyl, elaidyl, eicosyl, isostearyl, as well as a residue obtained by eliminating a hydroxyl group from a higher alcohol such as a C1–C36 linear or branched, saturated or unsaturated alcohol which is obtainable by an oxo process, Ziegler process, or a Guerbet process.

$A^1$ and $A^2$ represents C2–C3 linear or branched alkylene groups. "a" and "b" denote the average addition mol numbers of alkylene oxide, and they represent a number from 0 to 20 inclusive. "a" and "b" are each preferably from 0 to 5, and particularly preferably 0. The $A^1$s in the number of "a" and the $A^2$s in the number of "b" may be identical or different from one another.

X and Y represent halogen. Examples of x and Y include chlorine, bromine, and iodine, of which chlorine is preferred.

In the alcohols and alcoholates of formula (3) which are used in the methods of the present invention, $R^6$ represents C1–C36 linear or branched alkyl or C2–C36 alkenyl groups. $R^6$ is preferably C1–C18 alkyl or C2–C18 alkenyl, and more preferably C1–C4 alkyl. Specific examples of such alkyl or alkenyl groups include methyl, ethyl, propyl, isopropyl, butyl, pentyl, hexyl, 2-ethylhexyl, heptyl, octyl, nonyl, decyl, undecyl, dodecyl, tridecyl, tetradecyl, pentadecyl, hexadecyl, heptadecyl, octadecyl, oleyl, elaidyl, eicosyl, isostearyl, as well as a residue obtained by eliminating a hydroxyl group from a higher alcohol such as a C1–C36 linear or branched, saturated or unsaturated alcohol which is obtainable by an oxo process, Ziegler process, or a Guerbet process. Particularly, methyl, ethyl, propyl, isopropyl, and butyl are preferred.

$A^3$ represents C2–C3 linear or branched alkylene groups. "d" denotes the average addition mol number of alkylene oxide, representing a number from 0 to 20 inclusive. "d" is preferably from 0 to 5, and particularly preferably 0. The $A^3$s in the number of "d" may be identical or different from one another.

M represents a hydrogen atom, alkali metal elements such as Na, K, or Li, or alkaline earth metal elements such as Ca. M is preferably alkali metal or alkaline earth metal, and particularly preferably alkali metal.

The alkyl phosphoric halide of formula (2) which is used in method (i) of the present invention can be obtained by reacting a phosphorus oxyhalide of formula (5) with a first organic hydroxyl compound of formula (6) or with a mixture of the first organic hydroxyl compound and a second organic hydroxyl compound of formula (7) in the presence of an organic amine. However, in order to obtain phosphoric triesters with high purity, method (ii) is recommended, in which phosphorus oxyhalide and an organic hydroxyl compound are first reacted and then a hydrochloric salt of organic amine is removed.

The phosphorus oxyhalide of formula (5) used in the present invention is preferably phosphorus oxychloride. Examples of the organic hydroxyl compounds of formula (6) or (7) include alcohols having alkyls or alkenyls represented by $R^4$ and $R^5$.

The alkyl phosphoric halide of formula (2) which is used in method (i) of the present invention may be obtained by any known method. For example, 1 mol of phosphorus oxyhalide is reacted with 0.8 to 2.2 mol of an organic hydroxyl compound for 2 to 16 hours at a reaction temperature of –50 to 50° C. Examples of organic amines which can be used in this reaction include triethylamine, tripropylamine, tributylamine, pyridine, and picoline.

In order to remove hydrochloric acid salts of amines after reaction of phosphorus oxyhalide and organic hydroxyl compounds, washing, filtration, centrifugal separation, etc. may be suitably applied.

In method (ii) of the present invention, the reaction of alkyl phosphoric halide of formula (2) (which is obtained by removing a hydrochloric acid salt of amine after reaction of phosphorus oxyhalide and an organic hydroxyl compound) and a alcohol or alcoholate of formula (3) may be carried out by either adding an alcohol or alcoholate to alkyl phosphoric halide or adding alkyl phosphoric halide to an alcohol or alcoholate. Preferably, alkyl phosphoric halide is added to an alcohol or alcoholate. That is, method (iii) is preferred in which method (i) and method (ii) are combined.

The alkyl phosphoric halide of formula (2) of the present invention may be used as is or in a solution form in an organic solvent. The organic solvent is not particularly limited insofar as it is inert to the reaction and is capable of dissolving alkyl phosphoric halides. Examples of proper solvents include aliphatic hydrocarbons such as hexane, heptane, and octane; alicyclic hydrocarbons such as cyclopentane, cyclohexane, and methylcyclohexane; and aromatic hydrocarbons such as benzene, toluene, xylene, and ethylbenzene, and ethers such as tetrahydrofuran. These solvents may be used singly or in combinations of two or more.

Although either alcohol or alcoholate of formula (3) may be used interchangeably, alcoholate is more preferred. Commercially available alcoholates may be used. In view of industrial adequacy, an alcoholate in alcohol prepared by adding a hydroxide of alkali metal or alkaline earth metal to an alcohol is recommended. The alcohol preferably has an alkyl or alkenyl group which is identical to that possessed by the alcoholate. Hydroxides of alkali metal or alkaline earth metal are preferably sodium hydroxide, potassium hydroxide, lithium hydroxide, and calcium hydroxide. Particularly, alkali metal hydroxides, in particular sodium hydroxide and potassium hydroxide, are preferred. The amount of alcohol used for preparing an alcohol solution of alcoholate is preferably such an amount that is sufficient for dissolving the alcoholate. Specific amounts can be determined by the kinds of alcohol and alcoholate. For example, alcohol is preferably used in such an amount which falls between the amount (on a weight basis) equivalent to that of alkyl phosphoric halide and the amount 10 times that of the alkyl phosphoric halide.

When alcoholate is prepared by adding an alkyl phosphoric halide to an alcohol, water is by-produced. In the case where an alcohol such as butanol which is not miscible with water is used, water is preferably removed from the reaction system by azeotropic distillation.

In the reaction of an alkyl phosphoric halide of formula (2) of the present invention and an alcohol or alcoholate of formula (3), 1 mol of an alkyl phosphoric halide is reacted with 1.0 to 5.0 mol of an alcohol or alcoholate. The reaction temperature is not lower than 0° C., but not higher than the boiling point of alcohol, and is preferred to be kept in a range of 10 to 40° C. Although the reaction time is not particularly limited, it is preferably 1 to 5 hours, and more preferably 1 to 2 hours. After completion of reaction, excessive alcohol is distilled off, and inorganic salts are removed by filtration or similar methods. The resulting matter is washed with water, and dried. Thus, an asymmetric phosphoric triester of formula (4) having a high purity can be obtained at a high yield.

The amount of the phosphoric triester of formula (1) of the present invention to be incorporated into an external composition is not particularly limited. For example, when emulsion-type compositions are prepared, it is preferred that the triester be incorporated in an amount ranging from 0.001 to 90% by weight, and particularly from 1 to 50% by weight, of the total weight of the composition.

The external compositions of the present invention may be water-in-oil emulsions, oil-in-water emulsions, or oilbase preparations.

The external compositions of the present invention may be applied to the skin or the hair. Moreover, they may be medicinal compositions or cosmetic compositions. Preferably, the external compositions of the present invention are cosmetic compositions to be applied to the skin or the hair.

The forms of the external compositions of the present invention are not particularly limited. Examples of applicable forms include packs, foundations, lipsticks, skin detergents, shampoos, rinses, styling agents, hair nourishers, hair growing agents, and ointments. In addition to the phosphoric triester of formula (1), the external compositions of the invention may also contain optional components which are routinely used as components of external compositions. Examples of such optional components include oils, water, surfactants, humectants, UV-shielding agents, chelating agents, pH regulators, preservatives, thickeners, colorants, perfumes, and medicinal components. The medicinal components are not particularly limited. For example, analgetic/antiphlogistic agents, antipruriginous agents, bactericidal/disinfecting agents, astringents, skin ointments, hormones, and vitamins.

The present invention will next be described in detail by way of examples, which should not be construed as limiting the invention.

SYNTHETIC EXAMPLE 1

Synthesis of didodecylmethyl phosphate
(Compound 1a)

In a 1 liter four-neck flask equipped with a thermometer and a dropping funnel, 15.3 g (0.10 mol) of phosphorus oxychloride and 100 ml of tetrahydrofuran were placed. While cooling the flask in a water bath at a temperature of not higher than 30° C., a THF solution containing 37.2 g (0.20 mol) of dodecyl alcohol and 20.2 g (0.20 mol) of triethyl amine was added dropwise to the flask over a period of about one hour. After completion of addition, reaction was allowed to proceed for 4 hours at a temperature of not higher than 30° C. A hydrochloric acid salt of triethylamine was filtered off. 500 g of methanol were added to the residue, and mixed for 8 hours at 25° C. Ethyl acetate and water were added, followed by extraction and washing with water (a necessary amount of ethanol was added for demulsification). The organic layer was condensed to obtain 45.0 g of a pale yellow oil. The oil was purified by silica gel chromatography (solvent: hexane/ethyl acetate), obtaining 27.8 g (0.062 mol) of the target didodecylmethyl phosphate as a colorless transparent oil in a purity of not lower than 99%.

SYNTHETIC EXAMPLE 2

Synthesis of dialkyl (C13, C15) hexyl phosphate
(Compound 1b)

In a 1 liter four-neck flask equipped with a thermometer and a dropping funnel, 15.3 g (0.10 mol) of phosphorus oxychloride and 100 ml of hexane were placed. While cooling the flask in a water bath at a temperature of not higher than 30° C., a hexane solution containing 42.5 g (0.20 mol) of a (C13, C15) oxo alcohol [trademark: Diadol 135 (hydroxyl value: 212.4), manufactured by Mitsubishi Chemical industries Ltd.) and 20.2 g (0.20 mol) of triethylamine was added dropwise to the flask over a period of about one hour. After completion of addition, reaction was allowed to proceed for 4 hours at a temperature of not higher than 30° C. Ion exchange water was added and a hydrochloric acid salt of triethylamine was removed by washing with water. The residue was added dropwise, at 50° C., to 460 g of hexanol in which 4.0 g (0.1 mol) of sodium hydrochloride was dissolved. It was mixed for 1 hour. Hexane and water were added, followed by extraction and washing with water (a necessary amount of ethanol was added for demulsification). The organic layer was condensed to obtain 48.0 g of a pale yellow oil. The oil was purified by silica gel chromatography (solvent: hexane/ethyl acetate), obtaining 24.5 g (0.047 mol) of the target dialkyl (C13, C15) hexyl phosphate as a colorless transparent oil in a purity of not lower than 96%.

SYNTHETIC EXAMPLE 3

Synthesis of di-dodecylbutyl phosphate (Compound 1c)

In a 1 liter four-neck flask equipped with a thermometer and a dropping funnel, 15.3 g (0.10 mol) of phosphorus oxychloride and 100 ml of tetrahydrofuran were placed. While cooling the flask in a water bath at a temperature of not higher than 30° C., a THF solution containing 37.2 g (0.20 mol) of dodecyl alcohol and 20.2 g (0.20 mol) of triethylamine was added dropwise to the flask over a period of about one hour. After completion of addition, reaction was allowed to proceed for further 4 hours at a temperature of not higher than 30° C. A hydrochloric acid salt of triethylamine was filtered off. 450 g of butanol were added to the residue, and mixed for 48 hours at 25° C. Ethyl acetate and water were added, followed by extraction and washing with water (a necessary amount of ethanol was added for demulsification). The organic layer was condensed to obtain 47.5 g of a pale yellow oil. The oil was purified by silica gel chromatography (solvent: hexane/ethyl acetate), obtaining 22.8 g (0.046 mol) of the target di-dodecylbutyl phosphate as a colorless transparent oil in a purity of not lower than 96%.

SYNTHETIC EXAMPLE 4

Synthesis of diisostearyl ethyl phosphate (Compound 1d)

In a 1 liter four-neck flask equipped with a thermometer and a dropping funnel, 30.6 g (0.20 mol) of phosphorus oxychloride and 150 ml of hexane were placed. While cooling the flask in a water bath at a temperature of not higher than 30° C., a hexane solution containing 109 g (0.40 mol) of isostearyl alcohol and 40.4 g (0.40 mol) of triethylamine was added dropwise to the flask over a period of about one hour. After completion of addition, reaction was allowed to proceed for further 4 hours at a temperature of not higher than 30° C. A hydrochloric acid salt of triethylamine was filtered off. 460 g of ethanol was added to the residue, and mixed for 8 hours at 50° C. Ethyl acetate and water were added, followed by extraction and washing with water (a necessary amount of ethanol was added for demulsification). The organic layer was condensed to obtain 128 g of a pale yellow oil. The oil was purified by silica gel chromatography (solvent: hexane/ethyl acetate), obtaining 77.0 g (0.117 mol) of the target diisostearyl ethyl phosphate as a colorless transparent oil in a purity of not lower than 95%.

SYNTHETIC EXAMPLE 5

Synthesis of bis(2-heptylundecyl) ethyl phosphate (Compound 1e)

In a 1 liter four-neck flask equipped with a thermometer and a dropping funnel, 23.0 g (0.15 mol) of phosphorus oxychloride and 150 ml of tetrahydrofuran were placed. While cooling the flask in a water bath at a temperature of not higher than 30° C., a THF solution containing 81.6 g (0.30 mol) of 2-heptylundecyl alcohol and 30.3 g (0.30 mol) of triethylamine was added dropwise to the flask over a period of about one hour. After completion of addition, reaction was allowed to proceed for further 4 hours at a temperature of not higher than 5° C. A hydrochloric acid salt of triethylamine was filtered off. 230 g of ethanol were added to the residue, and mixed for 8 hours at 50° C. Ethyl acetate and water were added, followed by extraction and washing with water (a necessary amount of ethanol was added for demulsification). The organic layer was condensed to obtain 96.0 g of a pale yellow oil. The oil was purified by silica gel chromatography (solvent: hexane/ethyl acetate), obtaining 49.0 g (0.074 mol) of the target bis(2-heptylundecyl) ethyl phosphate in a purity of not lower than 96%.

SYNTHETIC EXAMPLE 6

Synthesis of dioleyl ethyl phosphate (Compound 1f)

In a 1 liter four-neck flask equipped with a thermometer and a dropping funnel, 15.3 g (0.10 mol) of phosphorus oxychloride and 100 ml of tetrahydrofuran were placed. While cooling the flask in a water bath at a temperature of not higher than 30° C., a THF solution containing 54.0 g (0.20 mol) of oleyl alcohol and 20.2 g (0.20 mol) of triethylamine was added dropwise to the flask over a period of about one hour. After completion of addition, reaction was allowed to proceed for further 4 hours at a temperature of not higher than 30° C. A hydrochloric acid salt of triethylamine was filtered off. 460 g of ethanol was added to the residue, and mixed for 24 hours at 25° C. Ethyl acetate and water were added, followed by extraction and washing with water (a necessary amount of ethanol was added for demulsification). The organic layer was condensed to obtain 46.0 g of a pale yellow oil. The oil was purified by silica gel chromatography (solvent: hexane/ethyl acetate), obtaining 30.1 g (0.046 mol) of the target dioleyl ethyl phosphate as a pale yellow oil in a purity of not lower than 95%.

SYNTHETIC EXAMPLE 7

Synthesis of dodecylisostearyl ethyl phosphate (Compound 1g)

In a 1 liter four-neck flask equipped with a thermometer and a dropping funnel, 15.3 g (0.10 mol) of phosphorus oxychloride and 100 ml of tetrahydrofuran were placed. While cooling the flask in a water bath at a temperature of not higher than 30° C., a THF solution containing 27.1 g (0.10 mol) of isostearyl alcohol and 10.1 g (0.10 mol) of triethylamine was added dropwise to the flask over a period of about one hour. After mixing for one hour, a THF solution containing 18.6 g (0.10 mol) of dodecyl alcohol and 10.1 g (0.10 mol) of triethylamine was added dropwise to the flask over a period of about one hour. After completion of addition, reaction was allowed to proceed for further 4 hours at a temperature of not higher than 30° C. A hydrochloric acid salt of triethylamine was filtered off. 230 g of ethanol were added to the residue, and mixed for 8 hours at 50° C. Ethyl acetate and water were added, followed by extraction and washing with water (a necessary amount of ethanol was added for demulsification). The organic layer was condensed to obtain 54.0 g of a pale yellow oil. The oil was purified by silica gel chromatography (solvent: hexane/ethyl acetate), obtaining 33.4 g (0.058 mol) of the target dodecylisostearyl ethyl phosphate in a purity of not lower than 90%.

SYNTHETIC EXAMPLE 8

Synthesis of (2-heptylundecyl) hexyl ethyl phosphate (Compound 1h)

In a 1 liter four-neck flask equipped with a thermometer and a dropping funnel, 23.0 g (0.15 mol) of phosphorus oxychloride and 150 ml of tetrahydrofuran were placed. While cooling the flask in a water bath at a temperature of not higher than 30° C., a THF solution containing 40.8 g (0.15 mol) of 2-heptylundecyl alcohol and 15.2 g (0.15 mol) of triethylamine was added dropwise to the flask over a period of about one hour. After completion of addition, reaction was allowed to proceed for further 2 hours at a temperature of not higher than 30° C. Subsequently, a THF solution containing 15.3 g (0.15 mol) of hexyl alcohol and 15.2 g (0.15 mol) of triethylamine was added dropwise over a period of about one hour. After completion of addition, reaction was allowed to proceed for further 6 hours at a temperature of not higher than 30° C. A hydrochloric acid salt of triethylamine was filtered off.

230 g of ethanol was added to the residue, and mixed for 8 hours at 50° C. Ethyl acetate and water were added, followed by extraction and washing with water (a necessary amount of ethanol was added for demulsification). The organic layer was condensed to obtain 63.0 g of a pale yellow oil. The oil was purified by silica gel chromatography (solvent: hexane/ethyl acetate), obtaining 32.2 g (0.070 mol) of the target (2-heptylundecyl) hexyl ethyl phosphate in a purity of not lower than 97%.

SYNTHETIC EXAMPLE 9

Synthesis of didodecyl cyclohexyl phosphate (Compound 1i)

In a 1 liter four-neck flask equipped with a thermometer and a dropping funnel, 15.3 g (0.10 mol) of phosphorus oxychloride and 100 ml of tetrahydrofuran were placed. While cooling the flask in a water bath at a temperature of not higher than 30° C., a THF solution containing 37.2 g (0.20 mol) of dodecyl alcohol and 20.2 g (0.20 mol) of triethylamine was added dropwise to the flask over a period of about one hour. After completion of addition, reaction was allowed to proceed for further 4 hours at a temperature of not higher than 30° C. A hydrochloric acid salt of triethylamine was filtered off. 460 g of cyclohexanol was added to the residue, and mixed for 24 hours at 60° C. Ethyl acetate and water were added, followed by extraction and washing with water (a necessary amount of ethanol was added for demulsification). The organic layer was condensed to obtain 48.5 g of a pale yellow oil. The oil was purified by silica gel chromatography (solvent: hexane/ethyl acetate), obtaining 20.6 g (0.040 mol) of the target didodecylcyclohexyl phosphate as a pale yellow oil in a purity of not lower than 96%.

SYNTHETIC EXAMPLE 10

Synthesis of (2-heptylundecyl) diphenyl phosphate (Compound 1j)

In a 1 liter four-neck flask equipped with a thermometer and a dropping funnel, 27.1 g (0.10 mol) of diphenylphosphoryl chloride and 100 ml of tetrahydrofuran were placed. While cooling the flask in a water bath at a temperature of not higher than 30° C., a THF solution containing 27.1 g (0.10 mol) of 2-heptylundecyl alcohol, 10.1 g (0.10 mol) of triethylamine, and 2.4 g (0.02 mol) of dimethylamino pyridine triethylamine was added dropwise to the flask over a period of about one hour. After mixing for one hour, the content of the flask was mixed for 48 hours at room temperature. Ethyl acetate and water were added, followed by extraction and washing with water (a necessary amount of ethanol was added for demulsification). The organic layer was condensed to obtain 43.5 g of a pale yellow oil. The oil was purified by silica gel chromatography (solvent: hexane/ethyl acetate), obtaining 21.8 g (0.043 mol) of the target (2-heptylundecyl)diphenyl phosphate in a purity of not lower than 96%.

The spectra of $^1$H-NMR and IR of compounds 1a to 1j synthesized in Synthetic Examples 1–10 are shown in Table 1.

TABLE 1

| Compound | IR ($\nu$ (cm$^{-1}$)) | $^1$H-NMR (CDCl$_3$, $\delta$ (ppm)) |
|---|---|---|
| 1a | 2932, 2860, 1467, 1281, 1035 | 0.88(t, 6H), 1.2–1.4(br, 36H), 1.70(t, 4H), 3.76(d, 3H), 4.03(dt, 4H) |
| 1b | 2932, 2860, 1467, 1266, 1029 | 0.90(t, 12H), 1.2–1.4(br, 48H), 1.6–1.9(br, 5H), 3.75–4.05(m, 6H) |
| 1c | 2932, 2860, 1467, 1281, 1023 | 0.88(t, 6H), 0.93(t, 3H), 1.2–1.4(br, 38H), 1.67(t, 6H), 4.02(dt, 6H) |
| 1d | 2932, 2860, 1464, 1278, 1029 | 0.85(t, 6H), 0.89(t, 6H), 1.2–1.4(br, 57H), 1.68(t, 4H), 4.02(dt, 4H), 4.11(dq, 2H) |
| 1e | 2932, 2860, 1467, 1269, 1020 | 0.89(t, 12H), 1.2–1.4(br, 59H), 1.64(m, 2H), 3.94(dd, 4H), 4.12(dq, 2H) |
| 1f | 2932, 2860, 1467, 1266, 1029 | 0.88(t, 6H), 1.2–1.4(br, 47H), 1.68(t, 4H), 1.7–2.4(br, 8H), 3.98(dd, 4H), 4.12(dq, 2H), 5.2–5.5(m, 4H) |
| 1g | 2932, 2860, 1467, 1266, 1029 | 0.85(t, 3H), 0.89(t, 3H), 1.2–1.4(br, 51H), 1.68(t, 4H), 4.02(dt, 4H), 4.11(dq, 2H) |
| 1h | 2932, 2860, 1467, 1278, 1029 | 0.86(t, 9H), 1.2–1.4(br, 37H), 1.6–1.9(br, 3H), 3.92(t, 2H), 4.03(dt, 2H), 4.12(dq, 2H) |
| 1i | 2932, 2860, 1467, 1266, 1029 | 0.88(t, 6H), 1.2–1.6(br, 42H), 1.7–2.0(m, 8H), 4.02(dt, 4H), 4.2–4.3(m, 1H) |
| 1j | 2932, 2860, 1464, 1269, 1029 | 0.89(t, 6H), 1.2–1.4(br, 28H), 1.64(m, 1H), 3.96(dd, 2H), 7.1–7.4(m, 10H) |

SYNTHETIC EXAMPLE 11

To 14.6 g (0.095 mol) of phosphorus oxychloride in hexane, 51.4 g (0.190 mol) of 2-heptylundecyl alcohol, 19.2 g (0.190 mol) of triethylamine in hexane were added dropwise while maintaining the temperature at not higher than 0° C. After ripening the mixture at 25° C., a hydrochloric acid salt of triethylamine was removed by washing. The solvent was also removed to obtain 59.1 g (0.095 mol) of bis(2-heptylundecyl) phosphoric chloride (not less than 95% purity was confirmed by $^{31}$-NMR)

4.56 g (0.114 mol; 1.2 times the amount by weight of phosphoric chloride) were added to 295 g of ethanol (five times the amount by weight of phosphoric chloride) to obtain sodium ethylate in ethanol, to which the thus-obtained phosphoric chloride was added dropwise at a temperature ranging from 20 to 30° C. After completion of reaction, the reaction was allowed to proceed for further 1 hour at a temperature range from 20 to 30° C. Excessive ethanol was distilled off. Inorganic salts were removed by filtration and washing, followed by drying. As a result, 58.4 g of bis(2-heptylundecyl)ethyl phosphate was obtained (yield: 97-%).

In $^{31}$P-NMR, any signal indicating the presence of by-products, diester phosphate and its pyro-modifications, was not observed, confirming that an asymmetric phosphoric triester with high purity was obtained.

SYNTHETIC EXAMPLE 12

The procedure of Synthetic Example 11 was repeated using 2-heptylundecyl phosphoric dichloride in place of bis(2-heptylundecyl) phosphoric chloride. As a result, the target compound, (2-heptylundecyl)diethyl phosphate was obtained at a yield of 98%.

In $^{31}$P-NMR, any signal indicating the presence of by-products, diester phosphate and its pyro-modifications, was not observed, confirming that an asymmetric phosphoric triester with high purity was obtained.

SYNTHETIC EXAMPLE 13

The procedure of Synthetic Example 11 was repeated using didodecyl phosphoric chloride in place of bis(2-heptylundecyl) phosphoric chloride. As a result, the target compound, didodecylethyl phosphate was obtained at a yield of 97%.

In $^{31}$P-NMR, any signal indicating the presence of by-products, diester phosphate and its pyro-modifications, was not observed, confirming that an asymmetric phosphoric triester with high purity was obtained.

SYNTHETIC EXAMPLE 14

The procedure of Synthetic Example 11 was repeated using sodium butylate obtained by azeotropic distillation of n-butanol and sodium hydroxide, in place of sodium ethylate in ethanol. As a result, the target compound, bis(2-heptylundecyl)butyl phosphate was obtained at a yield of 95%.

In $^{31}$P-NMR, any signal indicating the presence of by-products, diester phosphate and its pyro-modifications, was not observed, confirming that an asymmetric phosphoric triester with high purity was obtained.

SYNTHETIC EXAMPLE 15

The procedure of Synthetic Example 11 was repeated using a commercially obtained powdery sodium ethylate in ethanol in place of an ethanol solution of sodium ethylate obtained from ethanol and sodium hydroxide.

As a result, the target compound, bis(2-heptylundecyl) ethyl phosphate was obtained at a yield of 99%.

In $^{31}$P-NMR, any signal indicating the presence of by-products, diester phosphate and its pyro-modifications, was not observed, confirming that an asymmetric phosphoric triester with high purity was obtained.

SYNTHETIC EXAMPLE 16

The procedure of Synthetic Example 11 was repeated, except that bis(2-heptylundecyl)phosphoric chloride in hexane was added to sodium ethylate in ethanol to cause a reaction. As a result, the target compound, bis(2-heptylundecyl)ethyl phosphate was obtained at a yield of 96%.

In $^{31}$P-NMR, any signal indicating the presence of by-products, diester phosphate and its pyro-modifications, was not observed, confirming that an asymmetric phosphoric triester with high purity was obtained.

SYNTHETIC EXAMPLE 17

The procedure of Synthetic Example 11 was repeated, except that the amount of ethanol was the same as that of phosphoric chloride rather than 5 times that of phosphoric chloride. As a result, the target compound, bis(2-heptylundecyl)ethyl phosphate was obtained at a yield of 95%.

In $^{31}$P-NMR, any-signal indicating the presence of by-products, diester phosphate and its pyro-modifications, was not observed, confirming that an asymmetric phosphoric triester with high purity was obtained.

SYNTHETIC EXAMPLE 18

The procedure of Synthetic Example 11 was repeated by changing the phosphoric chloride from bis(2-heptylundecyl) phosphoric chloride to (2-heptylundecyl)hexyl phosphoric chloride. As a result, the target compound, (2-heptylundecyl)ethyl hexyl phosphate was obtained at a yield of 94%.

In $^{31}$P-NMR, any signal indicating the presence of by-products, diester phosphate and its pyro-modifications, was not observed, confirming that an asymmetric phosphoric triester with high purity was obtained.

SYNTHETIC EXAMPLE 19

The procedure of Synthetic Example 11 was repeated using ethanol in place of an ethanol solution of sodium ethylate obtained from ethanol and sodium hydroxide. Twenty four hours were needed to complete the reaction. The target compound, bis(2-heptylundecyl)ethyl phosphate was obtained at a yield of 96%.

In $^{31}$P-NMR, any signal indicating the presence of by-products, diester phosphate and its pyro-modifications, was not observed, confirming that an asymmetric phosphoric triester with high purity was obtained.

SYNTHETIC EXAMPLE 20

The procedure of Synthetic Example 11 was repeated except that sodium ethylate in ethanol was added to phosphoric chloride rather than phosphoric chloride was added to sodium ethylate in ethanol. As a result, the target compound, bis(2-heptylundecyl)ethyl phosphate was obtained at a yield of 94%.

In $^{31}$P-NMR, signals indicating the presence of by-products, diester phosphate and its pyro-modifications, were observed. From the ratio in area of signals accounting for asymmetric phosphoric triester and by-products, the purity of the obtained asymmetric phosphoric triester was found to be 86%.

SYNTHETIC EXAMPLE 21

The procedure of Synthetic Example 11 was repeated except that the phosphoric chloride from which a hydrochloric acid salt of triethylamine had not been removed was used in this Synthetic Example. The yield of the target compound, bis(2-heptylundecyl)ethyl phosphate, was 93%.

In $^{31}$P-NMR, signals indicating the presence of byproducts, diester phosphate and its pyro-modifications, were observed. From the ratio in area of signals accounting for asymmetric phosphoric triester and by-products, the purity of the obtained asymmetric phosphoric triester was found to be 82%.

SYNTHETIC EXAMPLE 22

The procedure of Synthetic Example 11 was repeated using bis(2-(2-hexyloxyethoxy)ethyl phosphoric chloride in place of bis(2-heptylundecyl)phosphoric chloride. The target compound, bis(2-(2-hexyloxyethoxy)ethyl) ethyl phosphate, was 97%.

In $^{31}$P-NMR, any signal indicating the presence of by-products, diester phosphate and its pyro-modifications, was not observed, confirming that an asymmetric phosphoric triester with high purity was obtained.

COMPARATIVE SYNTHETIC EXAMPLE 1

(Method described in Japanese Patent Application Laid-open (kokai) No. 4-41498)

To 25 g (0.163 mol) of phosphorus oxychloride in hexane, 88.2 g (0.326 mol) of 2-heptylundecyl alcohol and 33.0 g (0.326 mol) of triethylamine in hexane were added dropwise while maintaining the temperature at not higher than 0° C. After completion of addition, the reaction system was ripened at 25° C. 7.6 g (0.163 mol) of ethanol and 16.5 g (0.163 mol) of triethylamine were added thereto, and ripened for 17 hours at 50° C. A hydrochloric acid salt of triethylamine was removed by filtration. Hexane was distilled off, obtaining 98.8 g (0.095 mol) of bis(2-heptylundecyl)ethyl phosphate (yield 96%).

In $^{31}$P-NMR, signals indicating the presence of byproducts, diester phosphate and its pyro-modifications, were observed. From the ratio in area of signals accounting for asymmetric phosphoric triester and by-products, the purity of the obtained asymmetric phosphoric triester was found to be 66%, which was considerably lower than purities achieved in the above-described Synthetic Examples.

Test Examples

The hydrating ability, sensation during use, and irritation to the skin of the compounds 1a through 1j synthesized in Synthetic Example Nos. 1 to 10 above were evaluated. The results are shown in Table 2.

Hydrating Ability

Each compound was combined with water and then shaken over night at 25° C. The water content in the oil phase was determined by Karl Fischer's method. From the obtained water content, the solubility of water in each compound was calculated. The results are indicated by A, B, and C, which indicate the following:

A: not less than 1.5 wt %

B: not less than 0.5 wt % but less than 1.5 wt %

C: less than 0.5 wt %.

Sensation During Use

A panel of 10 experts actually used each compound and evaluated its sensation during use. Overall evaluations were made including compatibility with the skin, reduced oiliness, reduced stickiness, and moistened sensation.

A: 8 or more panelists among 10 answered "good"

B: 6–7 panelists among 10 answered "good"

C: 4–5 panelists among 10 answered "good"

D: 3 or less panelists among 10 answered "good"

Irritation to the Skin

Five guinea pigs were used. Each compound was prepared into a 10% liquid paraffin solution, and the solution was directly applied to the skin of the animals for four continuous days. On the following day, the status of the skin was evaluated and rated according to the following criteria.

A: no abnormalities—slight redness

B: slight redness—redness

C: redness—papules

D: redness and papules observed in almost all animals

TABLE 2

|  | Hydrating ability | Sensation during use | Irritation to the skin |
|---|---|---|---|
| Compound 1a | A | A | B |
| Compound 1b | B | A | A |
| Compound 1c | A | A | B |
| Compound 1d | A | A | A |
| Compound 1e | A | A | A |
| Compound 1f | A | A | A |
| Compound 1g | B | A | A |
| Compound 1h | A | A | A |
| Compound 1i | B | B | A |
| Compound 1j | B | B | A |
| Comparative Example (1) | B | B | C |
| Comparative Example (2) | C | C | A |
| Comparative Example (3) | A | A | D |

Note)
Comparative Example (1): Tris(2-ethylhexyl) phosphate
Comparative Example (2): Trihexadecyl phosphate
Comparative Example (3): Diethyl dodecyl phosphate

EXAMPLES 1–4 and COMPARATIVE EXAMPLES 1–3

Creams having the compositions shown in Table 3 were prepared. They were evaluated with respect to several features regarding practical use and effects in treating and preventing rough skin. The results are shown in Table 4.

TABLE 3

(% by weight)

|  |  | Examples | | | | Comparative Examples | | |
|---|---|---|---|---|---|---|---|---|
|  |  | 1 | 2 | 3 | 4 | 1 | 2 | 3 |
| (1) | Batyl alcohol | 2.0 | 2.0 | 2.0 | 2.0 | 2.0 | 2.0 | 2.0 |
| (2) | Cetanol | 2.0 | 2.0 | 2.0 | 2.0 | 2.0 | 2.0 | 2.0 |
| (3) | Comp. compound (4) | — | — | — | — | 2.0 | — | — |
| (4) | Comp. compound (5) | — | — | — | — | — | 2.0 | — |
| (5) | Comp. compound (6) | — | — | — | — | — | — | 2.0 |
| (6) | Compound 1b | 20.0 | — | — | — | — | — | — |
| (7) | Compound 1d | — | 20.0 | — | — | — | — | — |
| (8) | Compound 1e | — | — | 20.0 | — | — | — | — |
| (9) | Compound 1h | — | — | — | 20.0 | — | — | — |
| (10) | Sorbitan monooleate | 1.0 | 1.0 | 1.0 | 1.0 | 1.0 | 1.0 | 1.0 |
| (11) | POE(40) hydrogenated castor oil | 1.5 | 1.5 | 1.5 | 1.5 | 1.5 | 1.5 | 1.5 |
| (12) | Glycerol | 5.0 | 5.0 | 5.0 | 5.0 | 5.0 | 5.0 | 5.0 |
| (13) | Methyl paraben | 0.1 | 0.1 | 0.1 | 0.1 | 0.1 | 0.1 | 0.1 |
| (14) | Ethyl paraben | 0.1 | 0.1 | 0.1 | 0.1 | 0.1 | 0.1 | 0.1 |
| (15) | Perfume | 0.1 | 0.1 | 0.1 | 0.1 | 0.1 | 0.1 | 0.1 |
| (16) | Purified water | B | B | B | B | B | B | B |

Note)
B: balance
Comp. compound (4): Octyldodecyl myristate
Comp. compound (5): Olive oil
Comp. compound (6): Diglycerol diisostearate (Preparation method)

Oil phase components (1) to (11) were mixed and heated so that they dissolved. The temperature was maintained at 70° C. To this mixture, aqueous phase components (12) to (16) were added and emulsified in an emulsifier. The resulting emulsified product was cooled to a final temperature of 30° C. using a heat exchanger. The cooled material was packaged in a container to obtain a cream product.

(Preparation method)

Oil phase components (1) to (11) were mixed and heated so that they dissolved. The temperature was maintained at 70° C. To this mixture, aqueous phase components (12) to (16) were added and emulsified in an emulsifier. The resulting emulsified product was cooled to a final temperature of 30° C. using a heat exchanger. The cooled material was packaged in a container to obtain a cream product.

(Test method)

(1) Properties during practical use (panel test)

A panel of 10 experts actually used each cream and evaluated its properties during practical use.

Evaluation consisted of 4 items, i.e., compatibility with the skin, reduced stickiness, moistened sensation, and overall rating. The following criteria were used.

A: 8 or more panelists among 10 answered "good"

B: 6–7 panelists among 10 answered "good"

C: 4–5 panelists among 10 answered "good"

D: 3 or less panelists among 10 answered "good".

(2) Rough skin score

Ten women (age: 20–50) who had rough skin on the cheeks during winter used the creams. Two different creams were applied to the cheeks of each woman, one cream on one cheek, and the other cream on the other cheek, and they used the creams for 2 weeks. On the day following completion of the 2 week-application, their cheek skins were visually observed, and judgment was made according to the following criteria. Scores are mean values of actual data.

0: no rough skin

1: slightly rough skin

2: moderately rough skin

3: considerably rough skin

4: extraordinarily rough skin

TABLE 4

|  | Examples of Invention | | | | Comparative Examples | | |
| --- | --- | --- | --- | --- | --- | --- | --- |
|  | 1 | 2 | 2 | 4 | 1 | 2 | 3 |
| Test items for practical use | | | | | | | |
| Compatibility with the skin | A | A | A | A | B | C | B |
| Reduced stickiness | A | B | A | A | C | C | B |
| Moistened sensation | A | A | A | B | C | A | B |
| Overall evaluation | A | A | A | A | B | B | B |
| Skin roughness score | | | | | | | |
|  | 0.8 | 0.8 | 0.8 | 0.6 | 2.2 | 1.9 | 1.6 |

As is apparent from the above Table 4, the creams of the present invention have excellent skin care effects and compatibility with the skin.

EXAMPLES 5–7 and COMPARATIVE EXAMPLE 4

Emulsions having the compositions shown in Table 5 were prepared. They were evaluated with respect to several features regarding practical use and mildness to the skin.

The results are shown in Table 6.

TABLE 5

|  | Examples | | | Comparative Examples (% by weight) |
| --- | --- | --- | --- | --- |
|  | 5 | 6 | 7 | 4 |
| (1) Compound 1a | 5.0 | — | — | — |
| (2) Compound 1d | — | 5.0 | — | — |
| (3) Compound 1g | — | — | 5.0 | — |
| (4) Comp. compound (7) | — | — | — | 5.0 |
| (5) Squalane | 2.0 | 2.0 | 2.0 | 2.0 |
| (6) Batyl alcohol | 1.0 | 1.0 | 1.0 | 1.0 |
| (7) POE(40) hydrogenated castor oil | 1.5 | 1.5 | 1.5 | 1.5 |
| (8) Methyl paraben | 0.1 | 0.1 | 0.1 | 0.1 |
| (9) Ethyl paraben | 0.1 | 0.1 | 0.1 | 0.1 |
| (10) Ethanol | 3.0 | 3.0 | 3.0 | 3.0 |
| (11) Glycerol | 2.0 | 2.0 | 2.0 | 2.0 |
| (12) Perfume | 0.1 | 0.1 | 0.1 | 0.1 |
| (13) Purified water | B | B | B | B |

Note)
B: balance
Comp. compound (7): Octyldodecyl lactate (Preparation method)

Using the above ingredients, components (1) to (7) were mixed and heated so that they dissolved. The temperature was maintained at 70° C. Similarly, components (8) to (13) were heated and mixed and maintained at 70° C., to which the mixture of (1) to (7) was added and emulsified, obtaining an emulsion.

(Test method)

(1) Properties During Practical Use (Panel Test)

Properties during practical use were investigated in manners and criteria identical to those employed in Examples 1 to 4 and Comparative Examples 1 to 3.

(2) Skin Irritation Test

A closed patch test was performed on human upper arms (24 hours). The results were rated according to the following criteria. Scores are mean values of actual data.

0: no abnormalities

1: slight redness

2: redness

3: redness and papules

TABLE 6

|  | Examples | | | Comparative Examples |
| --- | --- | --- | --- | --- |
|  | 5 | 6 | 7 | 4 |
| Test items for practical use | | | | |
| Compatibility with the skin | A | A | A | C |
| Reduced stickiness | A | B | A | B |
| Moistened sensation | B | A | A | B |
| Overall evaluation | A | A | A | B |
| Skin irritation score | | | | |
|  | 0.8 | 0.2 | 0.4 | 1.4 |

EXAMPLE 8

Milky emulsion:

| | (% by weight) |
|---|---|
| Oil phase: | |
| Compound 1a | 8.0 |
| Squalane | 2.0 |
| Batyl alcohol | 1.0 |
| Sorbitan trioleate | 1.0 |
| POE (40) sorbitan monooleate | 1.0 |
| Ethyl paraben | 0.1 |
| Aqueous phase: | |
| Methyl paraben | 0.1 |
| Ethanol | 3.0 |
| Glycerol | 2.0 |
| Perfume | 0.1 |
| Purified water | balance |
| | 100.0 |

The above components were used. The oil phase components were mixed and heated to dissolve, and the temperature was maintained at 70° C. Similarly, the aqueous phase components were mixed and heated to dissolve at 70° C. To the resulting solution, the oil phase mixture was added and emulsified using an emulsifier. The emulsion was gradually cooled to obtain a milky emulsion.

EXAMPLE 9

Cream:

| | (% by weight) |
|---|---|
| Oil phase: | |
| Compound 1b | 20.0 |
| Octyldodecyl myristate | 5.0 |
| Cetanol | 2.0 |
| POE (20) sorbitan monostearate | 1.5 |
| Sorbitan monostearate | 0.5 |
| Carnauba wax | 2.0 |
| Butyl paraben | 0.1 |
| Aqueous phase: | |
| Glycerol | 3.0 |
| Methyl paraben | 0.2 |
| Perfume | 0.1 |
| Purified water | balance |
| | 100.0 |

The above components were used. The oil phase components were mixed and heated to dissolve, and the temperature was maintained at 80° C. Similarly, the aqueous phase components were mixed and heated to dissolve at 80° C. To the resulting solution, the oil phase mixture was added and emulsified using an emulsifier. The emulsion was gradually cooled to obtain a cream.

EXAMPLE 10

Two-layer liquid foundation:

| | % by weight |
|---|---|
| Oil phase components: | |
| Compound 1c | 10.0 |
| POE (10) hydrogenated castor oil | 0.5 |
| Dimethylpolysiloxane-polyalkylene copolymer | 0.5 |
| Powder components: | |
| Silicone-treated titanium dioxide | 3.0 |
| Silicone-treated sericite | 7.5 |
| Silicone-treated iron oxide | 1.5 |
| Aqueous phase components: | |
| Glycerol | 5.0 |
| Ethanol | 10.0 |
| Perfume | 0.1 |
| Purified water | balance |
| | 100.0 |

The above components were used. The oil phase components were uniformly mixed and powder components were sufficiently dispersed therein. To the resulting dispersion, a uniformly mixed aqueous phase was added and emulsified using an emulsifier, obtaining a two-layered liquid foundation.

EXAMPLE 11

Emulsion-type foundation:

| | (% by weight) |
|---|---|
| Oil phase components: | |
| Compound 1d | 5.0 |
| Compound 1e | 6.0 |
| POE (10) hydrogenated castor oil | 0.5 |
| Dextrin fatty acid ester | 2.0 |
| Glycerol mononostearate | 2.0 |
| Propylene glycol monolaurate | 1.0 |
| Powder components: | |
| Silicone-treated titanium dioxide | 6.0 |
| Silicone-treated sericite | 7.0 |
| Silicone-treated iron oxide | 2.0 |
| Aqueous phase components: | |
| Glycerol | 5.0 |
| Sorbitol | 0.5 |
| Methyl paraben | 0.2 |
| Perfume | 0.1 |
| Purified water | balance |
| | 100.0 |

The above components were used. The oil phase components were heated to dissolve, and the temperature was maintained at 80° C. The powder components were added and sufficiently dispersed. To the resulting dispersion, an aqueous phase uniformly mixed at 80° C. was added and emulsified using an emulsifier, obtaining an emulsion-type foundation.

EXAMPLE 12

Lipstick:

|  | (% by weight) |
|---|---|
| Base: | |
| Compound 1f | 30.0 |
| Castor oil | 20.0 |
| Batyl alcohol | 25.0 |
| Lanolin | 5.0 |
| Candelilla wax | 6.0 |
| Carnauba wax | 6.0 |
| Tocopherol | 0.2 |
| Propyl paraben | 0.2 |
| Coloring matter | |
| Titanium dioxide | 2.5 |
| Organic pigment | 5.0 |
| Perfume | 0.1 |
|  | 100.0 |

The above components were used. The base components were heated to melt and homogeneously mixed. Components of coloring matter was added, and kneaded using a roll mill until a uniform dispersion was obtained. The dispersion was re-melted, to which perfume was added. The mixture was deaerated and poured into a die. The die was rapidly chilled to solidify the content. The solid product was taken out of the die and put in a stick holder. After shaping the solid product, the surface was smoothed by passing through a flame, obtaining a lipstick.

EXAMPLE 13

Pack (peel-off type):

|  | (% by weight) |
|---|---|
| Oil phase components: | |
| Compound 1g | 3.0 |
| Isopropyl myristate | 1.0 |
| POE (10) hydrogenated castor oil | 1.0 |
| Powder components: | |
| Titanium dioxide | 10.0 |
| Kaolin | 2.0 |
| Aqueous phase components: | |
| Glycerol | 5.0 |
| Beegum | 1.0 |
| Ethanol | 6.0 |
| Perfume | 0.2 |
| Purified water | balance |
| Film-forming agents: | |
| Polyvinyl alcohol | 10.0 |
| Sodium alginate | 3.0 |
|  | 100.0 |

The above components were used. The aqueous phase components were heated to dissolve, and the temperature of the mixture was maintained at 70° C. Similarly, the oil phase components were mixed and heated at 70° C. The resulting mixture was added to the aqueous phase and emulsified using an emulsifier. Powder components and filmforming agents were added and mixed. The emulsion was slowly cooled to obtain a pack.

EXAMPLE 14

Two-layer cosmetic water:

|  | (% by weight) |
|---|---|
| Aqueous phase components: | |
| Glycerol | 5.0 |
| Colorant | suitable amount |
| Purified water | balance |
| Oil phase components: | |
| Ethanol | 10.0 |
| Compound (1h) | 8.0 |
| POE (20) stearyl ether | 1.5 |
| POE (20) sorbitan monopalmitate | 0.5 |
| Ethylparaben | 0.1 |
|  | 100.0 |

Glycerol and colorant were added to purified water. Separately, ethanol, compound (1h), surfactant, ethyl paraben, and perfume were blended and mixed at room temperature. The latter mixture was added to the aqueous phase, and filtered while stirring to obtain a cosmetic water.

EXAMPLE 15

Hair tonic:

|  | (% by weight) |
|---|---|
| Compound 1i | 2.0 |
| Menthol | 0.2 |
| Fungicide (piroctone auramine) | 0.1 |
| Methyl nicotinate | 0.1 |
| Ethanol | 45.0 |
| Purified water | balance |
|  | 100.0 |

The above ingredients were heated to dissolve at 70° C., and then cooled to obtain a hair tonic.

EXAMPLE 16

|  | (% by weight) |
|---|---|
| Hair rinse: | |
| Distearyldimethylammonium chloride | 2.0 |
| Polyoxyethylene cetyl ether | 2.0 |
| 2-heptylundecanol | 1.0 |
| Compound 1j | 3.0 |
| Glycerol | 2.0 |
| Methyl paraben | 0.1 |
| Ethyl paraben | 0.1 |
| Perfume | 0.1 |
| Purified water | balance |
|  | 100.0 |

To 70° C. purified water, methyl paraben and perfume were added to dissolve. To the resulting solution, the remainder components which had been mixed and heated at 70° C. were added for emulsification. The emulsion was slowly cooled to obtain a hair rinse.

EXAMPLE 17

| | (% by weight) |
|---|---|
| Medicated cream: | |
| (1) Dexamethazone | 0.025 |
| (2) Propylene glycol | 8.0 |
| (3) Glycerol | 5.0 |
| (4) Liquid paraffin | 1.0 |
| (5) Compound 1d | 3.0 |
| (6) Fatty acid alkanolamide | 1.8 |
| (7) Sorbitan monooleate | 1.0 |
| (8) Glycerol monofatty acid ester | 1.5 |
| (9) Preservative | suitable amount |
| (10) Clay mineral (bentonite) | 6.0 |
| (11) Purified water | balance |

Components (1), (4), (8), and (9) were added to component (5), mixed and heated at 70° C. to dissolve. This mixture is referred to as composition A. Part of component (11) was combined with (6) and (7) to dissolve, to which (2) and (3) were further added. This mixture is referred to as composition B. While stirring the composition B, the composition A was added to the composition B dropwise at 70° C. to perform preliminary emulsification. After that the mixture was emulsified using a homomixer.

The emulsion was slowly added to a dispersion prepared by adding (10) to the remainder part of (11) while stirring, after which the mixture was cooled to obtain a cream.

The compositions obtained in Examples 8 to 17 exhibited excellent sensation during use, and good compatibility with the skin or the hair. In addition, they are very safe and stable.

EXAMPLE 18

| | (% by weight) |
|---|---|
| Shampoo: | |
| Laurylether sulfate, sodium salt (EO = 3) | 15.0 |
| Amidepropylbetaine laurate | 3.0 |
| Decanoic acid monoglyceride | 2.0 |
| Compound 1e | 2.0 |
| Water | balance |
| | 100.0 |

A shampoo having the above composition was prepared by a routine method. The resulting shampoo had excellent detergency, caused reduced irritation, and had remarkable conditioning effects.

EXAMPLE 19

| | (% by weight) |
|---|---|
| Rinse-in-shampoo: | |
| Polyoxyethylene (20) laurylether | 10.0 |
| Amidepropylbetaine laurate | 5.0 |
| Trimethylstearyl ammonium chloride | 2.0 |
| Silicone emulsion (BY22-029, manufactured by Toray Dow Corning) | 1.0 |
| Compound 1d | 2.0 |
| Water | balance |
| | 100.0 |

A rinse-in-shampoo having the above composition was prepared by a routine method. The resulting product had excellent detergency, foam-producing ability, and rinsing effects.

EXAMPLE 20

| | (% by weight) |
|---|---|
| Body shampoo: | |
| Polyoxyethylene (20) lauryl ether | 15.0 |
| Lauroyl diethanolamide | 3.0 |
| Decanoic acid monoglyceride | 2.0 |
| Sodium laurate | 2.0 |
| Sodium myristate | 1.5 |
| Compound 1d | 2.0 |
| Water | balance |
| | 100.0 |

A body shampoo having the above composition was prepared by a routine method. The resulting body shampoo had excellent detergency, foam-producing ability, and rinsing ability. In addition, it exhibited enhanced skin moisturizing effects.

EXAMPLE 21

| | (% by weight) |
|---|---|
| Cleanser (gel) | |
| (1) Polyoxyethylene (20) octyldodecyl ether | 15.0 |
| (2) Glycerol | 10.0 |
| (3) Sorbitol | 10.0 |
| (4) Tri-2-ethylhexanoic acid triglyceride | 15.0 |
| (5) Liquid paraffin (K-230) | 5.0 |
| (6) Compound 1h | 10.0 |
| (7) Water | balance |
| | 100.0 |

The above components were used. Components (1) to (6) were mixed and heated to 70–80° C. to dissolve. After the mixture was cooled to 50° C., (7) was added while stirring. The resulting cleanser product excellently removed make-up dirts" making the after-wash skin moistened with excellent sensation.

EXAMPLE 22

| | (% by weight) |
|---|---|
| Facial detergent: | |
| Emanone 1112 (product of Kao corporation) | 10.0 |
| Potassium laurate | 5.0 |
| Potassium myristate | 3.0 |
| Potassium palmitate | 1.0 |
| Stearic acid | 1.0 |
| Glycerol | 15.0 |
| Sorbitol | 5.0 |
| 1,3-Butylene glycol | 5.0 |
| Lauric acid diethanolamide | 2.0 |
| Compound 1d | 2.0 |
| Water | balance |
| | 100.0 |

A facial detergent having the above composition was prepared by a routine method. The resulting product had excellent detergency and remarkable skin care effects, causing almost no tense feeling to the skin.

The phosphoric triesters of formula (1) have excellent compatibility with the skin, and irrespective of their high polarity, they have low viscosities and low melting points. In addition, they are very safe and stable. Accordingly, external compositions of the present invention containing the phosphoric triesters also have excellent compatibility with the skin, good sensation during use, and a high degree of safety.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A phosphoric triester having the formula (I):

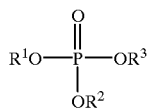

(1)

wherein $R^1$ is a C13–C20 branched alkyl or linear alkenyl, $R^2$ is C11–C18 linear or branched alkyl or C11–C18 linear alkenyl, and $R^3$ is C1–C6 linear, branched or cyclic alkyl.

2. The phosphoric triester according to claim 1, wherein, in formula (1), $R^3$ is ethyl.

3. The phosphoric triester according to claim 1 wherein $R^1$ is C16–C20 branched alkyl.

4. The phosphoric triester according to claim 3, wherein $R^1$ is selected from the group consisting of isostearyl, oleyl and 2-heptylundecyl.

5. The phosphoric triester according to claim 1, wherein $R^2$ is selected from the group consisting of isostearyl, oleyl and 2-heptylundecyl.

6. The phosphoric triester according to claim 1, wherein $R^3$ is selected from the group consisting of methyl, ethyl, n-propyl, n-butyl, n-pentyl, n-hexyl, isopropyl, isobutyl, sec-butyl, tert-butyl, cyclopentyl and cyclohexyl.

7. An external composition, comprising:
a) a phosphoric triester having the formula (I):

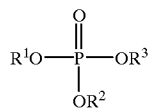

(1)

wherein $R^1$ is a C13–C20 branched alkyl or linear alkenyl, $R^2$ is C11–C18 linear or branched alkyl or C11–C18 linear alkenyl, and $R^3$ is C1–C6 linear, branched or cyclic alkyl; and
b) a cosmetically acceptable carrier.

8. The external composition according to claim 7 wherein, in formula (1), $R^3$ is ethyl.

9. A skin or hair applying composition comprising the external composition according to claim 7.

10. A skin or hair cosmetic composition comprising the external composition according to claim 7.

11. The external composition according to claim 7, wherein $R^1$ is C16–C20 branched alkyl.

12. The external composition according to claim 11, wherein $R^1$ is selected from the group consisting of isostearyl, oleyl and 2-heptylundecyl.

13. The external composition according to claim 7, wherein $R^2$ is selected from the group consisting of isostearyl, oleyl and 2-hepthylundecyl.

14. The external composition according to claim 7, wherein $R^3$ is selected from the group consisting of methyl, ethyl, n-propyl, n-butyl, n-pentyl, n-hexyl, isopropyl, isobutyl, sec-butyl, tert-butyl, cyclopentyl and cyclohexyl.

15. The external composition according to claim 7, which is in a form of a water-in-oil emulsion, oil-in-water emulsion or oil base preparation.

16. The external composition according to claim 7, wherein said phosphoric triester is present in an amount of about 0.001 to 90% by weight.

17. The external composition according to claim 12, which further comprises oils, water, surfactants, humectants, UV-shielding agents, chelating agents, pH regulators, preservatives, thickeners, colorants, perfumes and medicinal components.

* * * * *